United States Patent [19]
Rao et al.

[11] Patent Number: 5,837,690
[45] Date of Patent: *Nov. 17, 1998

[54] DERIVATIVES OF TRITERPENOID ACIDS AND USES THEREOF.

[75] Inventors: Narasinga Rao, Alameda; Mark Brian Anderson, Orinda; John Henry Musser, San Carlos, all of Calif.

[73] Assignee: Glycomed Incorporated, Alameda, Calif.

[*] Notice: The portion of the term of this patent subsequent to Aug. 9, 2013, has been disclaimed.

[21] Appl. No.: 465,893

[22] Filed: Jun. 6, 1995

Related U.S. Application Data

[62] Division of Ser. No. 049,018, Apr. 16, 1993, Pat. No. 5,527,980.

[51] Int. Cl.$^6$ ..................... A61K 31/705; A61K 51/04; G01N 33/53
[52] U.S. Cl. ..................... 514/26; 424/1.45; 424/9.1; 435/7.1; 514/885
[58] Field of Search ........................... 514/26, 885, 889; 536/5; 435/7.1; 424/1.45, 9.1

[56] References Cited

U.S. PATENT DOCUMENTS

| | | | |
|---|---|---|---|
| 3,070,623 | 12/1962 | Bazendale et al. | 260/468.5 |
| 3,070,624 | 12/1962 | Baxendale et al. | 260/468.5 |
| 3,934,027 | 1/1976 | Hans-Jurgen et al. | 536/309 |
| 4,173,648 | 11/1979 | Pifferi et al. | 424/309 |
| 5,147,859 | 9/1992 | Bombardelli et al. | 514/26 |
| 5,229,378 | 7/1993 | Ogata et al. | 514/99 |
| 5,268,364 | 12/1993 | Kojima et al. | 514/25 |
| 5,356,880 | 10/1994 | Kurono et al. | 514/26 |
| 5,519,008 | 5/1996 | Rao et al. | 514/26 |
| 5,527,890 | 6/1996 | Rao et al. | 536/5 |
| 5,545,623 | 8/1996 | Matsumori | 514/26 |

FOREIGN PATENT DOCUMENTS

| | | |
|---|---|---|
| 0518533 | 5/1992 | European Pat. Off. . |
| 515159A1 | 11/1992 | European Pat. Off. . |
| 518533A1 | 12/1992 | European Pat. Off. . |
| 04290846 | 10/1992 | Japan . |
| 068296 | 10/1992 | Japan . |
| 12991A1 | 8/1992 | WIPO . |
| 09129A1 | 5/1993 | WIPO . |

OTHER PUBLICATIONS

Ahmad et al., A New Triterpene Glycowide from the Roots of Symphytum Officinale, CA SELECTS® Carbohydrates (Chemical Aspects), *J. Natl. Prod.*, pp. 2–3 (1993).

Allevi et al., *J. Chem. Soc. Perkin Trans, I*, pp. 1275–1280 (1989).

Allevi et al., *J. Chem. Soc. Chem. Commun.*, pp. 101–102 (1987).

Allevi et al., *J. Chem. Soc. Chem. Commun.*, pp. 1245–1246 (1987).

Bertozzi et al., Antibody Targeting to Bacterial Cells Using Receptor–Specific Ligand/A Receptor–Mediated Immune Response Using Synthetic Glyconjugates, *J. Am. Chem. Soc.*, 114:2242–5543 (1992).

Bevilacqua et al., Endothelial Leukocyte Adhersion Molecule 1: An Inducible Receptor for Neutrophils Related to Complement Regulatory Proteins and Lectins, *Science*, 243:1160–1165 (1989).

Borel et al., Molluscicidal Saponins from Swartzia Madagascariensis Desvaux, *Helvetica Chimica Acta*, 70:571–576 (1987).

Campsteyn et al., Crystal and Molecular Structure of Glycyrrhetinic Acid Acetone Monohydrate, *Acta Cryst.*, B33:3443–3448 (1977).

Davidson et al., Glycyrrhetinic Acid Derivatives; A mNovel Class of Inhibitors of Gap–Junctional Intercellular Communication, Structure–Activity Relationships, *Journal of Pharmacology and Experimental Therapeutics*, 246:3:1104–1107 (1988).

Ding et al., Constituents of Leguminous Plants, CA SELECTS® Carbohydrates (Chemical Aspects), *Fac. Pharm. Sci.*, p. 11 (1993).

Doll et al., Clinical Trial of a Triterpenoid Liquorice Compound in Gastric and Duodenal Ulcer, *Lancet*, 11:793 (1962).

Egan et al., Inhibition of Mammaliam 5–Lipoxygenase by Aromatic Disulfides, *J. Biol. Chem.* 260:11554–11559 (1985).

Goekjian et al., *J. Org. Chem.*, vol. 56, pp. 6412–6422 (1991).

Grudzinskas et al., Prostaglandins and Congeners IV. The Synthesis of Certain 11–Substituted Derivatives of 11–Deoxyprostaglandin $E_2$ and $F_{2\alpha}$ From 15–O–Actylprostaglandin $A_2$ Methyl Ester, *Tetrahedron Lett*, 2:141–144 (1973).

Gundel et al., Endothelial Leukocyte Adhesion Molecule–1 Mediates Antigen–Induced Acute Airway Inflammation and Late–Phase Airway Obstruction in Monkeys, *J. Clin. Invest.*, 88:1407–1411 (1991).

Harris et al., Cellular and Biochemical Characterization of the Anti–Inflammatory Effects of DuP 654 in the Archidonic Acid Murine Skin Inflammation Model, *Skin Pharmacol.*, 3:29–40 (1990).

(List continued on next page.)

Primary Examiner—John Kight
Assistant Examiner—Howard C. Lee
Attorney, Agent, or Firm—Lyon & Lyon LLP

[57] ABSTRACT

Triterpenoid acid derivatives are described that exhibit dual pharmacophobic activities, specifically selectin ligand and leukotriene biosynthetic inhibitory activities, and that thus have significant applications for the treatment or prevention of certain diseases including cancer and diseases associated with the inflammatory process as well as applications for the diagnosis of disease.

20 Claims, 1 Drawing Sheet

OTHER PUBLICATIONS

Hirabayashi et al., Antiviral Activities of Glycyrrhizin and Its Modified Compounds Against Human Immunodeficient Virus Type 1 (HIV–1) and Herpes Simplex Virus Type 1 (HSV–1) In Vitro, *Chem. Pharm. Bull.*, 39(1):112–115 (1991).

Inoue et al., Inhibitory Effect of Glycyrrhetinic Acid Derivatives on Lipoxygenase and Protaglandin Synthetase, *Chem. Pharm. Bull.*, 2:897–901 (1986).

Lasky et al., Cloning of a Lymphocyte Homing Receptor Reveals a Lectin Domain, *Cell*, 56:1045–1055 (1989).

Levy et al., Cell Adhesion and Carbohydrates, *Annual Reports in Medicine Chemistry*, 29 (in press).

Mulligan et al., Protective Effects of Oligosaccharides in P–Selectin–Dependent Lung Injury, *Nature*, 364:149–151 (1993).

Mulligan et al., Role of Endothelial–Leukocyte Adhesion Molecule 1 (ELAM–1) in Neutrophil–Mediated Lung Injury in Rats, *J. Clin. Invest.*, 88:1396–1406 (1991).

Romussi et al., Revised Structures of Triterpene Saponins from Anchusa Officinalis L, CA SELECTS® Carbohydrates (Chemical Aspects), *Pharmazie*, p. 4 (1993).

Schaub et al., Prostaglandins and Congeners II. The Conjugate Addition of 3–t–Butoxyoctyl Magnesium Bromide to Clycopentenone. A Synthesis of RAC 11–Deoxy–14–Dihydroprostaglandin–$E_1$, *Tetrahedron Lett*, 2:129–130 (1973).

Springer et al., *Nature*, vol. 349, pp. 196–197 (1991).

Tedder et al., Isolation and Chromosomal Localization of cDNAs Encoding a Novel Human Lymphocyte Cell Surface Molecule, LAM–1, *J. Exp. Med*, 170–123–131 (1989).

Tyrrell et al., *Proc. Natl. Acad. Sci. USA*, vol. 88, pp. 10372–10376 (1991).

Yamada et al., Total Synthesis of Intensely Sweet Saponin, Osladin, CA SELECT® Carbohydrates (Chemical Aspects), *Fac. Pharm. Sci.*, p. 5 (1993).

DERIVATIVES OF TRITERPENOID ACIDS AND USES THEREOF.

This is a Divisional of application Ser. No. 08/049,018 filed on Apr. 16, 1993, now U.S. Pat. No. 5,527,890.

FIELD OF THE INVENTION

This invention relates generally to the field of medicinal chemistry. More specifically, it relates to derivatives of triterpenoid acids, preferably derivatives of glycyrrhetinic acid, that have dual pharmacophoric properties, formulations containing such and their use to prevent or treat certain diseases.

BACKGROUND OF THE INVENTION

Glycyrrhetinic acid, a member of the triterpenoid class of natural products, and certain derivatives thereof are known to have anti-ulcer, anti-inflammatory, antiallergic, antihepatitis and antiviral actions. For instance, certain glycyrrhetinic acid derivatives can prevent or heal gastric ulcers. Doll, R. et al., *Lancet* (1962) 11:793. Among such compounds known in the art are carbenoxolone (U.S. Pat. No. 3,070,623), glycyrrhetinic acid ester derivatives having substituents at the 3-O position (U.S. Pat. No. 3,070,624), amino acid salts of glycyrrhetinic acid (Japanese Patent Publication JP-A-44-32798), amide derivatives of glycyrrhetinic acid (Belgian Patent No. 753773), amide derivatives of 11-deoxoglycyrrhetinic acid (British Patent No. 1346871), cicloxolone (*Journal of Antimicrobial Chemotherapy*, (1986) 18:B:1845–200), and glycyrrhizic acid and its derivatives (*Chem. Pharm. Bull.* (1991) 39(1): 112–115).

Methods of making certain glycyrrhetinic acid compounds are also known. For example, methods of synthesizing 11-deoxoglycyrrhetinic acid, as well as its hemiester derivatives and its carboxylic acid and amide derivatives are also known. Japanese Patent Laid-Open Publication JP-A-59-70638; Japanese Patent Laid-pen Publication JP-A-58-8044; Japanese Patent Laid-Open Publication JP-A-63-135351.

Surprisingly, the biological mechanism(s) of action which accounts for the myriad medical activities of glycyrrhetinic acid and derivatives is not known. Glycyrrhetinic acid has been shown to inhibit enzymes involved in leukotriene biosynthesis, including 5-lipoxygenase activity, and this is thought to be responsible for its reported anti-inflammatory activity. Sotomatsu, S., et al., *Skin and Urology* (1959) 21:138 and Inoue, H., et al., *Chem. Pharm. Bull.* (1986) 2:897–901. Additional modes of action have not been reported for this class of compounds.

A large body of data has been accumulated that implicates a family of receptors, the selectins (or Lectin, EGF, Complement-Cellular Adhesion Molecules) (hereinafter LEC-CAMs) in certain diseases including cancer, arthritis, and in the inflammatory response. The three known members of this family, L-Selectin (LECAM-1, LAM-1, gp90MEL), E-Selectin (LECAM-2, ELAM-1) and P-Selectin (LECAM-3, GMP-140, PADGEM), each contain a domain with homology to the calcium-dependent lectins (C-lectins), an EGF-like domain, and several complement binding protein-like domains (Bevilacqua et al., *Science* (1989) 243:1160–1165; Johnston et al., *Cell* (1989) 56:1033–1044; Lasky et al., *Cell* (1989) 56:1045–1055; Tedder et al., *J. Exp. Med.* (1989) 170:123–133). Perhaps the most studied of the three selectins is E-selectin which is present on stimulated vascular endothelium, and is involved in neutrophil attachment prior to extravasation during an inflammatory response. It has been proposed that drugs that bind to the selectins will be useful medicaments for treating a variety of diseases.

In the field of medicinal chemistry it is desirable to identify and produce medicaments that have more than one mechanism of action that accounts for their medical utility. Clearly, it would be advantageous to a physician to have available, and be able to proscribe such medicaments because of their enhanced potency.

SUMMARY OF THE INVENTION

An important aspect of the invention is the discovery that certain derivatives of triterpenoid acids, preferably derivatives of glycyrrhetinic acid, exhibit dual pharmacophoric activity-selectin ligand activity and enzymatic inhibitory activity of leukotriene biosynthesis-consisting of a compound having the following general structural formula (I):

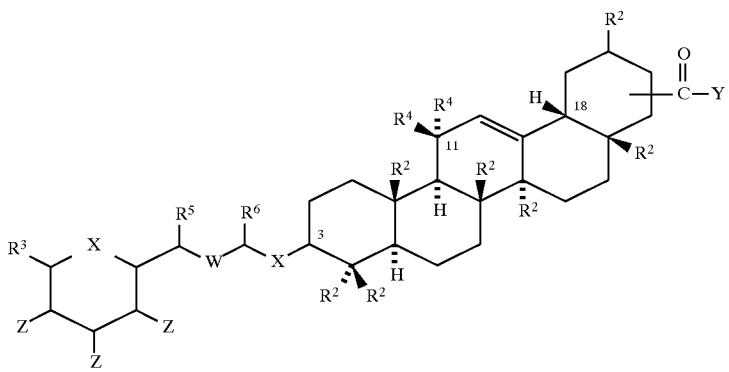

Wherein:
Y=$OR^1$, $NR^1_2$, O—$M^1$;
$R^1$=H, LOWER ALKYL,
$M^1$=$Na^+$, $K^+$, $Mg^{++}$, $Ca^{++}$ ions;
$R^2$=$CH_2OR_1$ or $CH_3$;
$R^3$=H, $CH_3$, lower alkyl, COY, $CH_2OH$, $CH_2OCH_2CH$=$CH_2$, $CH_2OSO$—$_3M^1$;
Z=$NR^1$, $NR^1Ac$, $NR^1Bz$, H, $OCH_3$, lower alkyl, OH, $SO_3$—$M^1$, $OCH_2CH$=$CH_2$, $OCH_2CO_2H$ or O-glucoside wherein a glucoside includes glucose, fucose, galactose, mannose, arabinose or xylose;
$R^4$=H, OH, $SO_3$—$M^1$, $NH(CH_2)_nNH^2$, or NH—Ph—$(NH_2)_n$ wherein n=1–8 and Ph is a phenyl or naphthyl ring substituted with up to 3 amine functionalities and the remaining substitutions can be H, $R^1$, $R^2$ or $CO_2R^1$;

or both $R^4$ taken together are oxo;

$R^5$ AND $R^1=R^6=H$, or taken together to form a 5 or 6 membered carbocyclic ring;

X=O,S, $NR^1_2$

W=C=O, C=$CR^1_2$, $CR^1CR^1_3$, $CR^1-CR^1_2OR^1$, $COR^1-CR^1OR^1_2$, $COR^1CR^1_2OR^1$, $CR^1CR^1_2NR^1_2$, $CR^1CR^1_2OCR^1COY$;

Another object of the invention is to provide a pharmaceutical formulation containing the compound of formula 1.

A third object of the invention is a method of enhancing the dual pharmacophoric activity of a triterpenoid compound consisting of binding a glucoside, directly or indirectly, to the 3 position of the triterpenoid.

A fourth object of the invention is a method to diagnosis disease by administering a compound of formula 1, such compound being suitably labelled to facilitate its location at a disease site in the body.

Other objects of the invention include, but are not restricted to, providing methods to treat diseases, which diseases include cancer, arthritis, and the inflammatory response.

These and other objects, advantages and features of the present invention will become apparent to those persons skilled in the art upon reading the details of the isolation, structure, formulation and usage of the invention compounds as more fully set forth below, references being made to the accompanying figures and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying drawings as follows.

DETAILED DESCRIPTION OF THE INVENTION

Figure 1:
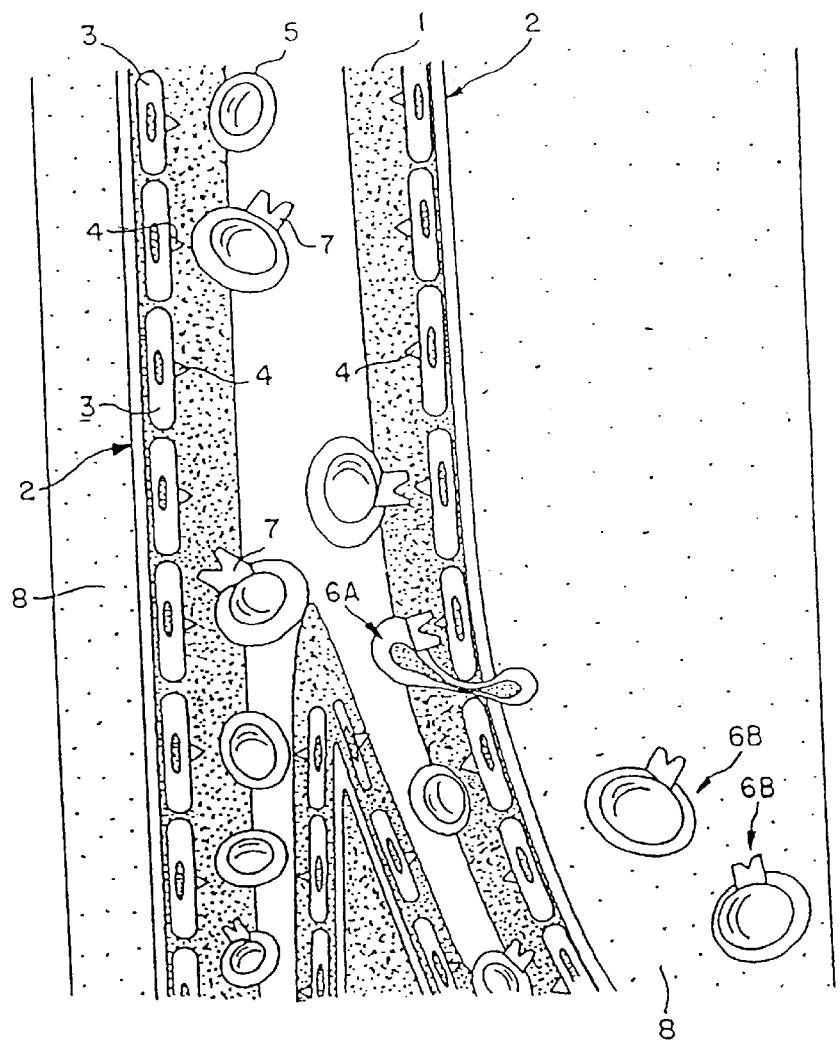
FIG. 1 is a cross-sectional schematic view showing the interaction between white blood cells and activated endothelial cells.

Throughout the description of the invention reference is made to certain publications including scientific articles and patents or patent applications. It is the intent that each of these publications be incorporated by reference when referred to in the specification.

It is to be further understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a ligand" includes mixtures of ligands, reference to "an ELAM-1" includes reference to mixtures of such molecules, reference to "the formulation" or "the method" includes one or more formulations, methods and/or steps of the type described herein and/or which will become apparent to those persons skilled in the art upon reading this disclosure and so forth.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein.

By "pharmacophore" is meant a compound that has a single biological activity with medical applications.

By "dual pharmacophore" or "dual pharmacophoric compound" is meant a compound that has two biological activities that contributes to and enhances the compounds medically useful applications, and includes of a triterpenoid and a glucoside, the glucoside being bound to the triterpenoid at the 3 position.

By glucoside is intended glucose, fucose, galactose, mannose, arabinose, xylose and chemically related sugars.

Some standard abbreviations used in connection with the present invention include: BSA, bovine serum albumin; DEAE, diethylaminoethyl; DMSO, dimethylsulfoxide; ELAM-1, endothelial/leukocyte adhesion molecule-1; HPTLC, high performance thin layer chromatography; LECAM-1, leukocyte/endothelial cell adhesion molecule-1; 5-LO, 5-lipoxygenase; MOPS, 3-[N-Morpholino] propanesulfonic acid; NANA, N-acetylneuraminic acid; PVC, polyvinylchloride; TLC, thin layer chromatography; TFA, trifluoroacetic acid; Tris, tris (hydroxymethyl) aminomethane.

General Overview

An unexpected property of the invention compounds is that these compounds exhibit dual pharmacophoric activity. More specifically, these compounds can act both as selectin ligands and inhibitors of leukotriene biosynthesis. Without intending to be bound to either particular mechanism of action that may account for the prophylactic or therapeutic effects of the invention compounds, Applicants nevertheless believe that both of these activities enhances and accounts for their medical uses.

Regarding a possible selectin mechanism of action, reference is now made to FIG. 1, which presents a cross-sectional view of a blood vessel 1.

The vessel wall 2 is lined internally with endothelial cells 3. The endothelial cells 3 can be activated causing the cells 3 to synthesize ELAM-1 which is displayed in FIG. 2 as a triangular surface receptor 4. Both red blood cells 5 and white blood cells 6 flow in the vessel 1. The white blood cells 6 display carbohydrate ligands 7 which have chemical and physical characteristics which allow the ligands 7 to bind to the receptors 4. Once the ligand 7 binds to the receptor 4, the white blood cell 6 is brought through the vessel wall 2 as is shown with the white blood cell 6A. The white blood cells 6B brought into the surrounding tissue 8 can have positive effects, such as fighting infection, and negative effects, such as inflammation.

Figure 2:
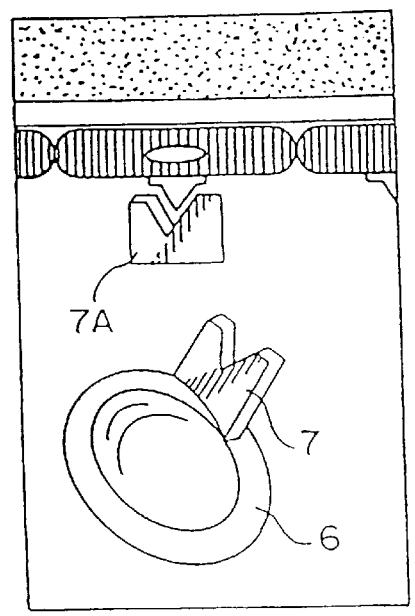
FIG. 2 is a cross-sectional schematic view showing how ligands of the invention might be used as pharmaceuticals to block ELAM-1.

Thus, as will be discussed more in detail below, and now by reference to FIG. 2, an important aspect of the present invention is that the inventors have produced compounds that act as selectin ligands 7 apart from their presence on the surface of white blood cells 6. These isolated ligands 7A adhere to ELAM-1 by themselves and can be formulated into pharmaceutical compositions, which when administered will effectively block the ELAM-1 and prevent the adhesion of a receptor 7 connected to a white blood cell 6. By administering pharmaceutically effective amounts of ligands 7A, some, but not all, of the white blood cells will not reach the surrounding tissue 8. By slowing the rate at which the white blood cells reach the surrounding tissue, inflammation can be prevented and/or alleviated.

For certain cancers to successfully spread throughout a persons body cell-cell adhesion must take place. This adhesion can be interrupted by the administration of compounds of the present invention which generally aid in blocking cell-cell adhesion. Accordingly, compounds of the invention can be used to retard the spread of cancer cells which display receptors which adhere to a compound of formula I.

As mentioned above, a second and unexpected property of the invention compounds is that these compounds are inhibitors of enzymes involved in leukotriene biosynthesis, including the enzyme 5-lipoxygenase. Leukotrienes are very potent chemokinetic and chemotactic agents which are thought to be involved in initiating the inflammatory response. Compounds that prevent leukotriene synthesis would be medically useful to treat certain diseases. Thus, the medicinal activity of the invention compounds may be attributed, at least in part, to their leukotriene biosynthetic inhibitory activity.

Testing Triterpenoid Acid Derivatives-Selectin Ligand Activity and Leukotriene Biosynthesis Inhibition Derivatives of triterpenoid acids encompassed by general structural formula I can be tested in accordance with one or more assay procedures in order to determine either their selectin binding properties as ligands for one or more of the selectins, or their capacity to inhibit one or more of the enzymes involved in the biosynthesis of leukotrienes. Compounds that have these activities would be encompassed by the present invention and thus be useful alone, or as part of a pharmaceutical composition which would be used to treat or prevent certain diseases.

Selectin binding assays can take several formats including cell based assays that employ cells which express the desired cell surface selectin receptor. Foxall, C. et al., *Journal of Cell Biology* (1992) 117:895–902. Such cells are used as probes to screen compounds by determining if the compounds adhere to the cells under assay conditions known to those skilled in the art. Alternatively, Elisa based assays can be utilized to identify invention compounds that bind to a chosen selectin. Such assays are described by Watson, S. R., C. Fennie, and L. A. Lasky, *Nature* (1991) 349:164–167; Watson, S. R., Y. Imai, C. Fennie, J. Geoffrey, M. Singer, S. D. Rosen, L. A. Lasky. *J. Cell Biol.* (1991) 115:235–243; or Watson, S. R., Y. Imai, C. Fennie, J. S. Geoffrey, S. D. Rosen, L. A. Lasky. *J. Cell Biol.* (1991) 110:2221–2229, and Foxall, C. et al., *Journal of Cell Biology*, 117:895–902 (1992).

Several assays can be performed to assess the inhibitory activity of the invention compounds against enzymes involved in leukotriene biosynthesis. For instance, leukotriene biosynthesis from arachidonic acid commences with 5-lipoxygenase oxidation of arachidonic acid to form 5-hydroperoxyeicosatetraenoic acid (5-HPETE), and in turn, leukotriene $A_4$ and 5-hydroxyeicosatetraenoic acid (5-HETE). Assays for 5-lipoxygenase are known in the art and can be readily performed as described by Shimuzu, T., et al., *Proc. Natl. Acad. Sci. USA* (1984) 81:693–698; and Epan, R., et al., *J. Biol. Chem.* (1985) 260:11554–11559.

Alternatively, 5-lipoxygenase and 12-lipoxygenase can be assayed by the method of Koshihara, M. et al., *J. Biol. Chem.* (1982) 257:7302. Cyclooxygenase activity can be assayed similarly using modified assay conditions as described by Inoue, H., et al., *Chem. Pharm. Bull.* (1986) 2:897–901.

Specific details of carrying out the appropriate assays for either selectin binding activity or leukotriene enzymatic inhibitory activity are described below.

After appropriate compounds are identified that have one or both of the above described activities these compounds can, if desired, be formulated into a pharmaceutical composition by combining the compounds with pharmaceutically acceptable excipient materials. Such compositions can be administered to a patient by intravenous injection, topical application, etc., in an amount sufficient to prevent or treat disease. Putative ELAM-1 ligands may be indentifed using Recombinantly Produced receptors. As mentioned above, the invention compounds can be screened for selectin ligand activity using a cell based assay. An example of one such assay wherein the invention compounds are assayed for ELAM-1 ligand activity initially consists of obtaining a complete cDNA for the ELAM-1 receptor obtained by PCR starting with total RNA isolated from IL-1 stimulated human umbilical vein endothelium. The resulting cDNA was inserted into the CDM8 plasmid (see Aruffo, A., and Seed, B., *Proc. Natl. Acad. Sci. USA* (1987) 84:8573) and the plasmid amplified in *E. coli*. Plasmid DNA from individual colonies was isolated and used to transfect COS cells. Positive plasmids were selected by their ability to generate COS cells that support HL-60 cell adhesion. DNA sequencing positively identified one of these clones as encoding for ELAM-1 (Bevilacqua, M.P., et al., *Science* (1989) 243:1160; Polte, T., et al., *Nucleic Acids Res.* (1990) 18:1083; Hession, C., et al., *Proc. Natl. Acad. Sci. USA* (1990) 87:1673). These publications are incorporated herein by reference for their disclosure of ELAM-1 and genetic material coding for its production. The complete nucleotide sequence of the ELAM-1 cDNA and predicted amino acid sequence of the ELAM-1 protein are given in the above cited article by Bevilacqua et al., which DNA and amino acid sequences are incorporated herein by reference (see also published PCT patent application WO90/13300 which was published Nov. 15, 1990, and which is incorporated herein by reference).

COS cells, expressing membrane-bound ELAM-1, were metabolically radiolabeled with $^{32}PO_4$ and used as probes in two assay systems to screen for recognition of triterpenoid acid derivatives. In the first, triterpenoid acid derivatives were adsorbed to the bottoms of PVC microtiter wells, while in the second they were resolved on TLC plates. In both assays these triterpenoid acid derivatives were probed for their ability to support adhesion of ELAM-transfected COS cells, untransfected COS cells, or COS cells transfected with a plasmid containing an irrelevant cDNA, under conditions of controlled detachment force (see Swank-Hill, P., et al., *Anal. Biochem.* (1987) 183:27; and Blackburn, C.C., et al., *J. Biol. Chem.* (1986) 261:2873 each of which is incorporated herein by reference to disclose the details of such assaying methodology).

Conjugates

Considering the dual biological properties of the invention compounds, that is, selectin ligand and inhibitors of leukotriene biosynthesis, advantage can be taken of the former to target biologically active molecules to the selectins by attaching such molecules to the triterpenoid acid derivatives via known chemical linkers. U.S. Pat. No. 4,810,784; and U.S. Pat. No. 5,034,514. Any drug of choice could be used, but preferably non-steroidal anti-inflammatory drugs (NSAIDs) such as naproxen or ibuprofen would be bound to the ligand and administered systemically in smaller amounts than otherwise required while obtaining an equivalent or even greater anti-inflammatory effect at the site of inflammation. Other drugs which might be attached include, but are not limited to, antibiotics, vasodilators and analgesics. Depending on the chemical nature of the drug, it may be coupled directly to the linker, or indirectly via the addition of a suitable reactive moiety.

More preferably the drug would be attached to the invention compounds by an enzymatically cleavable linker. A preferred linker of this sort would be cleavable by enzymes present in significant levels at the disease site. For example, if it is desired to target the invention compounds and drug to a site of inflammation, an enzymatically cleavable linker would be chosen that is cleaved by enzymes produced and secreted by inflammatory cells thereby causing the release of the compound and drug at the site of inflammation.

This means of drug delivery would significantly reduce systemic effects associated with invention compounds and/or drugs that display toxicity when administered in free form but not as part of a conjugate. That is, although an invention compound-drug conjugate would circulate throughout the patient's body, the free compound or drug would be present only in high concentrations at the disease site, and thus would not exhibit a systemic effect, or have a much reduced effect compared to administration of free compound or drug. Thus, this method of administration affords a mechanism whereby high concentrations of compounds and drugs can be brought to bear at a site of disease with reduced systemic effects.

In addition to the aforementioned linkers, drugs may be attached to polymeric backbones which may be, but are not limited to, simple polymers, polymeric carbohydrates, including cyclodextrins, heparin or its derivatives, peptides, polymeric beads, etc.

Use and Administration

The triterpenoid acid derivatives compounds of the invention can be administered to a subject in need thereof to treat the subject by either prophylactically preventing disease or relieving it after it has begun. The invention compounds are preferably administered with a pharmaceutically acceptable carrier, the nature of the carrier dependant on the chemical properties of the compounds, including solubility properties, and/or the mode of administration. For example, if oral administration is desired, a solid carrier may be selected, and for I.V. administration a liquid salt solution carrier may be used.

The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the invention compounds directly in transdermal formulations with permeation enhancers such as DMSO. Other topical formulations can be administered to treat certain disease indications.

Typically, the compounds of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on the responsiveness of the patient. Other effective dosages can be readily determined by one of ordinary skill in the art through routine trials establishing dose response curves.

It is believed that the compounds of the present invention can be used to treat a wide range of diseases, including cancer, rheumatoid arthritis and multiple sclerosis. The compounds of the invention would be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot formed has often suffered damage. When the antithrombotic has removed the clot, the damaged tissue beneath the clot and other damaged tissue in the endothelial lining which has been deprived of oxygen, become activated. The activated endothelial cells then synthesize the ELAM-1 receptors within hours of the cells being damaged. The receptors are extended into the blood vessels where receptors adhere to glycolipid ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient. Thus, it will be appreciated that the invention compounds will be beneficial for the treatment of heart attacks by preventing neutrophil adhesion to heart tissue and the damage to the tissue that results therefrom.

In addition to treating patients suffering from the trauma resulting from heart attack, patients suffering from actual physical trauma could be treated with formulations of the invention in order to relieve the amount of inflammation and swelling which normally results after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The compounds of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The compounds of formula I can be mixed with compatible, pharmaceutically acceptable excipients.

Certain methods of preparing dosage forms of the invention compounds are known, or will be apparent, to those skilled in the art. See, e.g., Remington's Pharmaceutical Sciences, Mack Publishing Company, Easton, Pennsylvania, 17th edition, 1985. The composition or formulation to be administered will, in any event, contain a quantity of the compound adequate to achieve the desired state in the subject being treated. The various compounds of the present invention can be used by themselves or in combination with pharmaceutically acceptable excipient materials as described above.

Synthetic Strategy

Synthesis of the various glycyrrhetinic acid conjugates requires manipulation about the 3-position of the triterpene nucleus. Some of these manipulations involve a double inversion methodology about this center.

The compounds can be inverted from the β- to the α- i.e. the $C_3$-β-OH to the $C_3$-α-OH using the Mitsunobu method (Mitsunobu, O. Synthesis (1981), 1) followed by use of the herein described C-glycosidation procedures.

In some instances, a benzyl ester protecting group can be used for the protection of the E-ring carboxyl group, with subsequent removal will also provide reduction of the 11-carbonyl function to afford 11-deoxo-glycyrrhetinic acid conjugates. It is known that glycyrrhetinic acid and its derivatives have an aldosterone (DCA)-like activity and promote sodium retention and potassium excretion, which may induce edema, a decrease in serum potassium levels, a rise in blood pressure and myopathy. 11-Deoxo-glycyrrhetinic acid does not substantially show the DCA activity of the parent compound [Baren, J. S., et al., *J. Med. Chem.* (1974) 17(2):184–191]. Thus, in one operation, the various derivatives are converted to potentially more useful compounds. For example, hydrogenating over $PtO_2$ in acetic acid at ambient temperature for 3 days [Barton, D. H. R., et al. *J. Chem. Soc.* (C), (1968),1031] can selectively remove the 11-oxo to afford 11-deoxo-glycyrrhetinic acid conjugates.

Other Synthetic Aspects

The synthesis of other compounds containing alternate carbohydrates attached to the carbon linking arms for the glycoside conjugates are accomplished by usual glycosidation methods. Alternately, any carbohydrate unit being charged or uncharged and/or deoxygenated species can be formed using the carbon-glycosidation procedure given in this disclosure, but this disclosure does not exclude the analogs prepared from branched, linear or other forms of di-, tri- and polysaccharides or oligosaccharides or combinations. The derivatized carbon-glycoside can be further utilized as a linking group between a pyran ring and the spacer attached to the glycyrrhetinic acid nucleus by a selective protection methodology involving use of a 2'3'-benzylidene derivative (see Example 4) in which selective functionalization and/or glycosidation can be accomplished prior to deprotection. Thus, the various derivatives are converted to potentially more useful compounds.

Multivalent Forms Of The Invention Compounds

The affinity of the invention compounds for a selectin receptor can be enhanced by providing multiple copies of a desired compound in close proximity, preferably using a scaffolding structure provided by a carrier moiety. It has been shown that provision of such multiple valence structure with optimal spacing between the moieties dramatically improves binding to a receptor. (See, for example, Lee, Y. C. et al., *Biochem* (1984) 23:4255).

The multivalency and spacing can be controlled by selection of a suitable carrier moiety. Such moieties include molecular supports which contain a multiplicity of functional groups that can be reacted with functional groups associated with the compounds of the invention. A particularly preferred approach involves coupling of the compounds of the invention to amino groups of the carrier through reductive amination. Reductive amination is a particularly convenient way to couple aldehyde moieties to free amino groups by first forming the Schiff base and then treating the conjugate with a reducing agent, such as a hydride reducing agent. Typically, the amino group-bearing carrier is mixed with the carbohydrate moiety at about pH 9 and allowed to form the Schiff base; the solvents are typically evaporated and a reducing agent is added at high pH to complete the reaction.

Particularly convenient carrier moieties to obtain multivalent forms of the invention compounds include amines (e.g. $N(CH_2CH_2NH_2)_3$), proteins and peptides, particularly those containing lysyl residues which have w-amino groups available for binding. It is also useful to include in the peptide or protein at least one tyrosine residue, as these residues offer a convenient site for labeling, for example with radioactive iodine. A particularly convenient carrier to obtain a trivalent couple is the peptide Lys-Tyr-Lys. Complete reaction of the compounds of the invention with the free amino groups on this peptide results in a trivalent moiety. Thus, compounds of the invention of the general formula (I) may be used to make multivalent constructs:

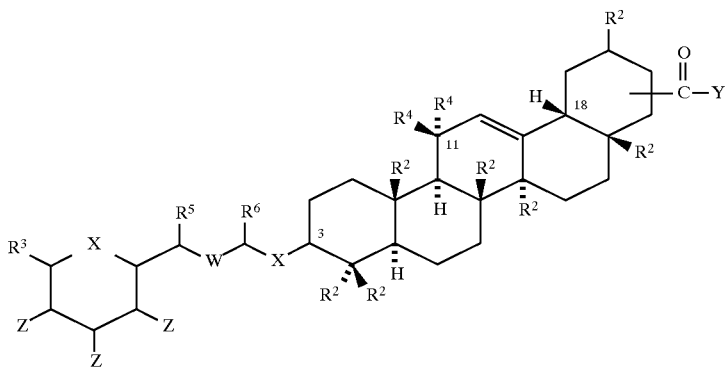

Attachments of the compounds to the amine, or vice versa, by reductive amination would produce multivalent compounds. Preferred attachment points would be at $R^3$, $R^4$, $R^5$, $R^6$, and X, and particularly at positions $R^3$, $R^5$ and $R^6$.

Of course, a variety of carriers can be used, including proteins such as BSA or HSA, a multiplicity of peptides including, for example, pentapeptides, decapeptides, pentadecapeptides, and the like. Preferably, the peptides or proteins contain the desired number of amino acid residues having free amino groups in their side chains; however, other functional groups, such as sulfhydryl groups or hydroxyl groups can also be used to obtain stable linkages. For example, the carbohydrate compounds of the invention may be oxidized to contain carboxyl groups which can then be derivatized with either free amino groups to form amides or with hydroxyl groups to form esters. In addition, a suitably functionalized biotin tether may be attached with subsequent complexation with avidin for multivalent forms.

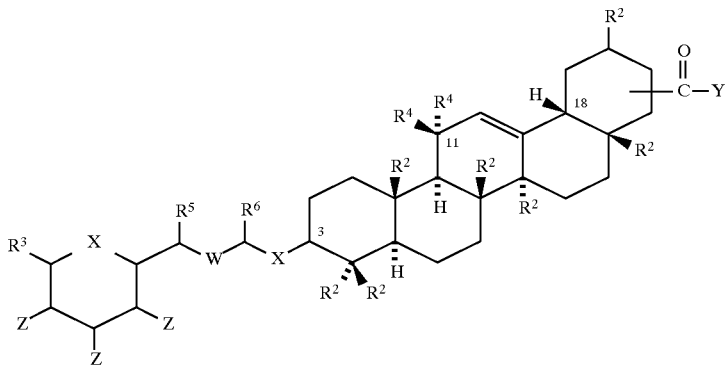

The structure of formula (I) above may be in different isomeric forms and such are encompassed by this disclosure. In particular the carbon glycoside moiety may be in either the alpha or beta configuration and the linkage by which any sugar is attached at the A-Ring C-3 position may be either axial or equatorial. However, here and throughout the different stereo configurations are not shown but are understood to be encompassed by this disclosure and the appended claims.

EXAMPLES

The following examples are put forth so as to provide those of ordinary skill in the art with a complete disclosure and description of how to make the compounds and compositions of the invention and are not intended to limit the scope of what the inventors regard as their invention. Efforts have been made to ensure accuracy with respect to numbers that would be used (e.g., amounts, temperature, etc.) but some experimental errors and deviations should be accounted for. Unless indicated otherwise, parts are parts by weight, molecular weight is weight average molecular weight, temperature is in degrees centigrade and pressure is at or near atmospheric.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

Experimental Section

General. Reagents were purchased from commercial suppliers such as Aldrich Chemical Company or Lancaster Synthesis Ltd. and were used without further purification unless otherwise indicated. Tetrahydrofuran (THF) and dimethylformamide (DMF) were purchased from Aldrich in sure seal bottles and used as received. All solvents were purified by using normal methods unless otherwise indicated. Reactions were done under a positive pressure of nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (tlc) was performed on glass-backed silica gel 60 F 254 plates Analtech (0.25 mm) and eluted with the appropriate solvent ratios (v/v) and are denoted where appropriate. The reactions were assayed by tlc and terminated as judged by the consumption of starting material.

Visualization of the tlc plates was done with a p-anisaldehyde spray reagent or phosphomolybdic acid reagent (Aldrich Chemical 20% wt in ethanol) and activated with heat.

Work-ups were typically done by doubling the reaction volume with the reaction solvent or extraction solvent and then washing with the indicated aqueous solutions using 25% by volume of the extraction volume unless otherwise indicated.

Product solutions were dried over $Na_2SO_4$ prior to filtration and evaporation of the solvents was performed under reduced pressure on a rotary evaporator and noted as solvents removed in vacuo.

Flash column chromatography (Still, W. C.; Kahn, M.; Mitra, A. J. Org. Chem. (1978) 43:2923) was done using Baker grade flash silica gel (47–61 mm) and a ratio of 50:1 unless otherwise stated.

Hydrogenations can be done at the pressure indicated in the examples, or at ambient pressure.

$^1$H-NMR spectra were recorded on a Varian 300 instrument operating at 300 MHz and $^{13}$C-NMR spectra were recorded on a Varian 300 instrument operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm) or internally tetramethylsilane (0.00 ppm) when appropriate. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz.

Infrared spectra were recorded on a Perkin-Elmer Fr-IR spectrometer as neat oils, or as $CDCl_3$ solutions, and are reported in wave numbers ($cm^{-1}$).

The mass spectra were obtained using FAB.

The yields indicated are yields of isolated products purified by flash chromatography and having a purity of greater than 95% as indicated by TLC and 300 MHz $^1$H-NMR.

Example 1

Preparation of Key Synthetic Intermediate 2-Chloromethyl-3-(tri-O-benzyl-α-L-C-fucopyranoside)-1-propene (1)

The following synthetic chemical intermediate compound that was used to prepare the final invention compounds was synthesized as now described.

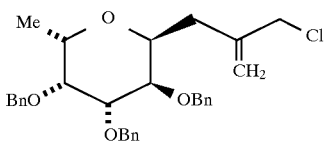

To a solution of tri-O-benzyl-L-fucopyranose (20.0 g, 46.03 mmole, 1.00 mmole eqiv.) in anhydrous acetonitrile (200 mL) at 0° C. was added 2-chloromethyl-3-trimethylsilyl-1-propene (30.0 g, 184.34 mmole, 4.00 mmole eqiv.). Trimethylsilane trifluoromethane sulfonic acid (10.24 g, 46.03 mmol, 1.00 mmole eqiv.) was added dropwise in anhydrous acetonitrile (30 mL, overall reaction concentration 0.2M) and the reaction contents stirred at 0° C. for 30 minutes. After 30 minutes, the reaction was diluted with ethyl acetate (230 mL) and the reaction was terminated by pouring the contents slowly into aqueous saturated sodium bicarbonate. The heterogeneous layers were separated and the organic phase was washed twice with portions of water, 1.0M hydrochloric acid and brine. The crude product was dried over anhydrous sodium sulfate, filtered and plugged through a small pad of silica gel. The solvent was removed in vacuo which afforded an oil that was chromatographed on Baker grade flash silica gel (47–61 mm) (ratio of 50 to 1) and eluted with 5 or 10% ethyl acetate in hexanes. Concentration in vacuo afforded 20.01 g of 2-Chloromethyl-3-(tri-O-benzyl-α-L-C-fucopyranoside)-1-propene (1) (85%).

Example 2

Preparation of 2-(tri-O-benzyl-α-L-C-methylfucopyranose)-3-[3-O-(18-β-Glycyrrhetinic acid)]-1-propene (2)

The following compound was prepared as follows.

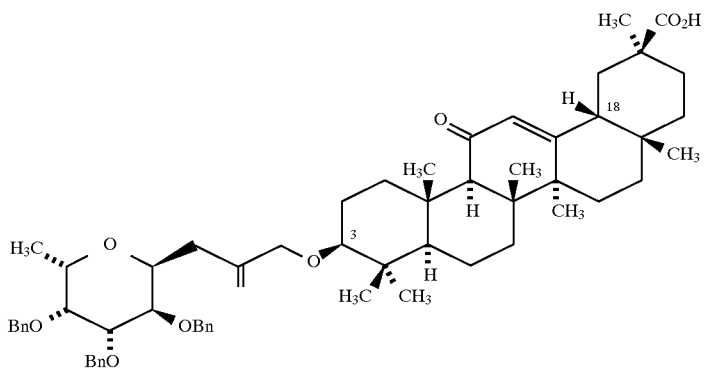

To a solution of sodium hydride (611 mg, 25.2 mmole, 6.00 mmole equiv.) in anhydrous 25% dimethylformamide in tetrahydrofuran (30 mL) at ambient temperature was added 18-β-glycyrrhetinic acid (2.00 g, 4.25 mmol, 1.00 mmole equiv.) in a minimum amount of anhydrous 25% dimethylformamide in tetrahydrofuran. Sodium iodide (6.37 g, 42.5 mmole, 10.00 mmole equiv.) and tetrabutylammonium iodide (157 mg. 0.425 mmole, 0.10 mmole equiv.) were added and the reaction contents were warmed to a gentle reflux (until the evolution of $H_2$ ceased) for 30 minutes. 2-Chloromethyl-3-(tri-O-benzyl-α-L-C-fucopyranoside)-1-propene (1) (6.47 g, 12.75 mmole, 3.00 mmole equiv.) was added dropwise in anhydrous 25% dimethylformamide in tetrahydrofuran (23 mL, total of 0.08M) and gently refluxed for 6 hours. After 6 hours at reflux, the reaction was terminated by the careful addition of 50% methanol in toluene (100 mL) at 0° C. and then 4M hydrochloric acid until the pH was 1–2 and then diluted with chloroform. The heterogeneous layers were separated and the organic phase was washed twice with portions of 1.0M hydrochloric acid, sodium bicarbonate and brine. The crude product was dried over anhydrous sodium sulfate, filtered and plugged through a small pad of silica gel eluting with ethyl acetate. The solvent was removed in vacuo which afforded an oil that was chromatographed on Baker grade flash silica gel (47–61 mm) (ratio 50 to 1) and eluted with benzene, 10% ethyl acetate in hexane, 30% ethyl acetate in hexane, 50% ethyl acetate in hexane, 100% ethyl acetate and finally with 50% methanol in chloroform. Concentration in vacuo afforded 2.80 g of 2-(tri-O-benzyl-α-L-C-methylfucopyranose)-3-[3-O-(18-β-Glycyrrhetinic acid)]-1-propene (2) (70%) as a white foam powder.

An alternate procedure to prepare 2-(tri-O-benzyl-α-L-C-methylfucopyranose)-3-[3-O-(18-β-Glycyrrhetinic acid)]-1-propene (2) is as follows. To a solution of sodium hydride (0.472 g, 19.68 mmole, 6.00 mmole equiv.) in anhydrous benzene (10 mL) at ambient temperature was added 18-β-glycyrrhetinic acid (1.547 g, 3.28 mmol, 1.00 mmole equiv.) dropwise in a minimum amount of anhydrous tetrahydrofuran. Sodium iodide (4.916 g, 32.8 mmole, 10.00 mmole equiv.) and tetrabutylammonium iodide (157 mg. 0.425 mmole, 0.10 mmole equiv.) were added and the reaction contents were warmed to reflux (until the evolution of H₂ ceased) for 30 minutes. 2-Chloromethyl-3-(tri-O-benzyl-α-L-C-fucopyranoside)-1-propene (1) (5.00 g, 9.86 mmole, 3.00 mmole equiv.) was added dropwise in anhydrous tetrahydrofuran (31 mL, total reaction concentration of 0.08M) and gently refluxed for 6 hours. After 6 hours at reflux, the reaction was terminated by the careful addition of 50% methanol in toluene (100 mL) at 0° C. and then 4M hydrochloric acid until the pH was 1–2 and the reaction contents were diluted with ethyl acetate. The heterogeneous layers were separated and the organic phase was washed twice with portions of 1.0M hydrochloric acid, saturated sodium thiosulfate and brine. The crude product was dried over anhydrous sodium sulfate, filtered and plugged through a small pad of silica gel and eluted with ethyl acetate. The solvent was removed in vacuo which afforded an oil that was chromatographed on Baker grade flash silica gel (47–61 mm) (ratio 50 to 1) and eluted with 10% ethyl acetate in hexane, 50% ethyl acetate in hexane, 100% ethyl acetate. Concentration in vacuo afforded 2.991 g of 2-(tri-O-benzyl-α-L-C-methylfucopyranose)-3-[3-O-(18-β-Glycyrrhetinic acid)]-1propene (2) (96%) as a white foam powder.

Example 3

Preparation of 1-[3-O-(18-β-Glycyrrhetinic acid)]-2-(α-L-C-methylfucopyranose)-propane (3)

The following compound was prepared as follows.

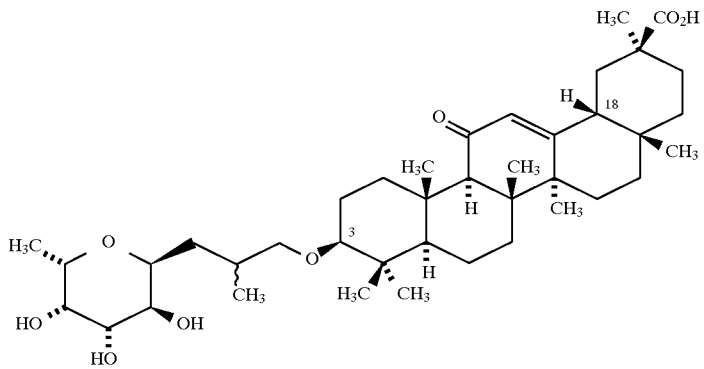

A solution of 2-(tri-O-benzyl-α-L-C-methylfucopyranose)-3-[3-O-(18-β-Glycyrrhetinic acid)]-1-propene (2) (15 mg, 0.0159 mmole, 1.00 mmole equiv.) in 10% acetic acid in methanol (ethyl acetate can be added to enhance solubility) (1.5 mL), was added to 10% palladium on carbon (35 mg per mmole of substrate) and placed on a Parr hydrogenation apparatus. The reaction vessel was evacuated and re-filled with hydrogen thrice and then shaken at 50 PSI for 48 hours. The reaction was terminated by filtering the contents through Celite to remove the catalyst. The produce was concentrated in vacuo and washed with dichloromethane to give a white powder to afford 10 mg of 1-[3-O-(18-β-Glycyrrhetinic acid)]-2-(α-L-C-methylfucopyranose)-propane (3) (99%).

Example 4

Preparation of 1-[3-O-(18-β-Glycyrrhetinic acid)]-2-(tri-O-benzyl-α-L-C-methyl-fucopyranose)-2',3'-propanediol (4)

The following compound was prepared as follows.

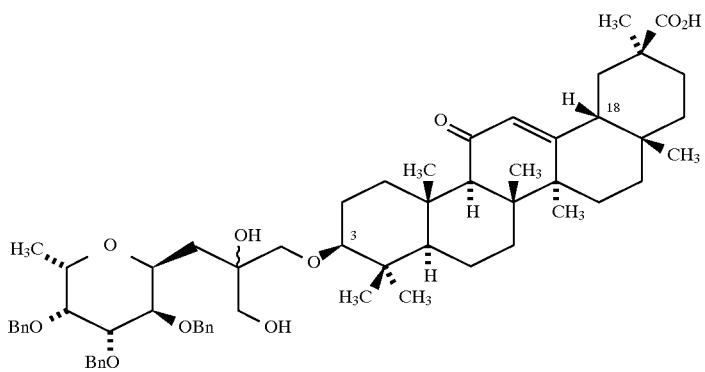

To a solution of 2-(tri-O-benzyl-α-L-C-methylfucopyranose)-3-[3-O-(18-β-Glycyrrhetinic acid)]-1-propene (2) (1.00 g, 1.06 mmole, 1.00 mmole equiv.) in anhydrous dichloromethane (5.3 mL, 0.2M) at ambient temperature was added osmium tetroxide (0.0106 mmole, 21.2 mL of a 0.5M solution in toluene, 0.01 mmole equiv.) and N-methylmorpholine-N-oxide (1.24 g, 10.6 mmole, 10.00 mmole eqiv.). The reaction contents were stirred at ambient temperature for 6 days and the reaction was terminated by the addition of 25% aqueous sodium metasulfite and stirred for 1 hour. The heterogeneous layers were separated and the organic phase was washed twice with portions of 25% aqueous sodium metasulfite, 1.0M hydrochloric acid, sodium bicarbonate and brine. The crude product was dried over anhydrous sodium sulfate, filtered and plugged through a small pad of silica gel. The solvent was removed in vacuo which afforded an oil that was chromatographed on Baker grade flash silica gel (47–61 mm) (ration of 50 to 1) and eluted with 50% ethyl acetate in hexane and then 5% methanol in chloroform. Concentration in vacuo afforded 837 mg of 1-[3-O-(18-β-Glycyrrhetinic acid)]-2-(tri-O-benzyl-α-L-C-methylfucopyranose)-2',3'-propanediol (4) (81%).

Example 5

Preparation of 1-[3-O-(18-β-Glycyrrhetinic acid)]-2-(α-L-C-methylfucopyranose)-2',3'-propanediol (5)

The following compound was prepared as follows.

1-[3-O-(18-β-Glycyrrhetinic acid)]-2-(tri-O-benzyl-α-L-C-methylfucopyranose)-2',3'-propanediol (4) (2.00 g, 2.05 mmole, 1.00 mmole equiv.) was dissolved in 10% acetic acid in methanol (10 mL, 0.2M), 10% palladium on carbon was added (35 mg per mmole of substrate wetted with toluene) placed on a Parr hydrogenation apparatus. The reaction vessel was evacuated and re-filled with hydrogen thrice and then shaken at 50 PSI for 48 hours. The reaction was terminated by filtering the contents through Celite to remove the catalyst. Concentration in vacuo afforded 1-[3-O-(18-β-Glycyrrhetinic acid)]-2-(α-L-C-methylfucopyranose)-2',3'-propanediol (5) as a white powder which was filtered and rinsed with dichloromethane to give 1.20 g (83%).

A further manipulation of a glycerol linking arm is necessary to give a 3'-O-glycosylated derivative. This can be accomplished by using the partial protection method developed by Garegg and Hultberg [Garegg, P. J., Hultberg, H., Carbo. Res. 93 (1981) C10–C11.] involving reductive ring opening of a 2',3'-benzylidene acetal with sodium cyanoborohydride in THF.

Acetates and benzoates serve as protecting groups for the hydroxyl groups in sugars and display neighboring group participation in glycosidation reactions. Thus, by judicious choice of protecting groups prior to the glycosidation, i.e., benzyl ethers, acetates or benzoates, one can preferentially select for either the alpha- or beta-carbon linked glycosides (H. Paulsen, ANGEW Chem. Int. Ed. Engl. (1982)21:155; R. R. Schmidt, "Synthesis of Carbon linked glycosides in Comprehensive Organic Synthesis", Ed. B. M. Trost, 6:33–64).

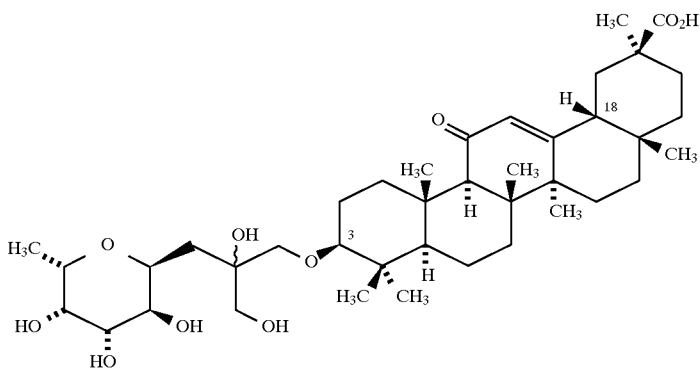

Example 6

Preparation of 1-[3-O-(18-β-Glycyrrhetinic acid)]-2-(α-L-C-methylfucopyranose)-2',3'-propanediol pentasulfate (6)

The following compound would be prepared as follows:

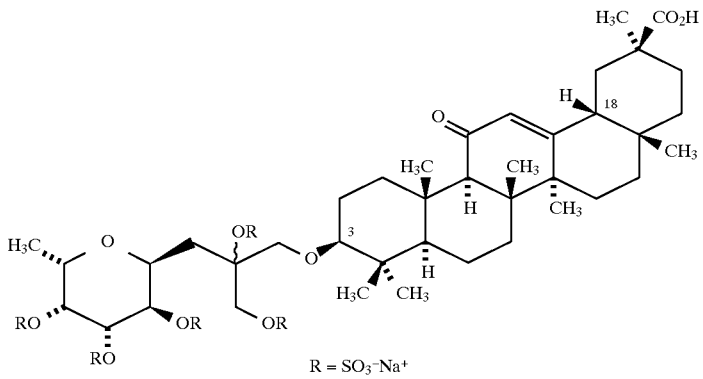

To a solution of 1-[3-O-(18-β-Glycyrrhetinic acid)]-2-(α-L-C-methylfucopyranose)-2',3'-propanediol (5) (50 mg, 0.709 mmole, 1.00 mmole equiv.) in anhydrous dimethylformamide (3.5 mL, 0.2M) at ambient temperature is added sulfur trioxide pyridine complex polymer bound (141.8 mmole, 10 mmole equiv.). The reaction contents are stirred at ambient temperature and then warmed to a gentle reflux for 8 hours. The reaction is terminated by cooling to ambient temperature and filtering the polymer through celite. The solvent is removed in vacuo which affords an oil that is azeotrophed with toluene. Concentration in vacuo affords 1-[3-O-(18-β-Glycyrrhetinic acid)]-2-(α-L-C-methylfucopyranose)-2',3'-propanediol pentasulfate (6). Reference:Graf, W. Chem. Ind. (1987) 232.

An alternate procedure to prepare 1-[3-O-(18-β-Glycyrrhetinic acid)]-2-(α-L-C-methylfucopyranose)-2',3'-propanediol pentasulfate (6) is as follows. To a solution of 1-[3-O-(18-β-Glycyrrhetinic acid)]-2-(α-L-C-methylfucopyranose)-2',3'-propanediol (5) (50 mg, 0.709 mmole, 1.00 mmole equiv.) in anhydrous dimethylformamide (3.5 mL, 0.2M) at ambient temperature is added sulfur trioxide pyridine complex (mmole, 10 mmole equiv.). The reaction contents are stirred at ambient temperature and then warmed to a gentle reflux for 8 hours. The reaction is terminated by cooling to ambient temperature. The solvent is removed in vacuo which affords an oil that is azeotrophed with toluene. Concentration in vacuo affords 1-[3-O-(18-β-Glycyrrhetinic acid)]-2-(α-L-C-methylfucopyranose)-2',3'-propanediol pentasulfate (6).

Example 7

Preparation of 1-[3-O-(18-β-Glycyrrhetinic acid)]-2-oxo-2-(tri-O-benzyl-α-L-C-methylfucopyranose)-ethane (7)

The following compound was prepared as follows:

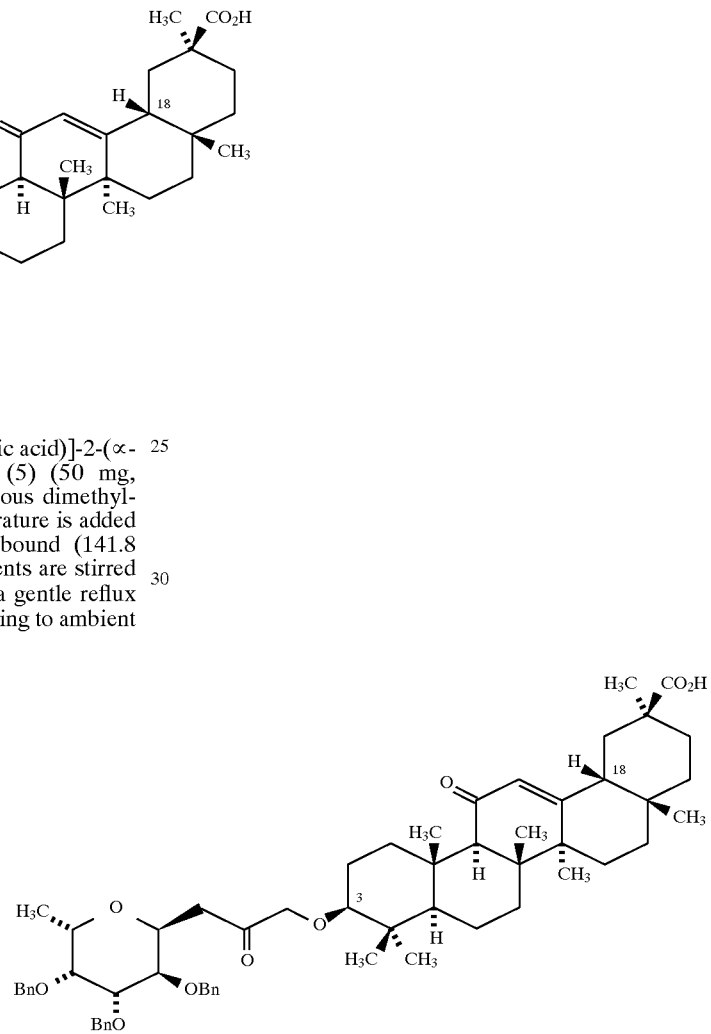

To a solution of 2-[3-O-(18-β-Glycyrrhetinic acid)]-3-(tri-O-benzyl-(α-L-C-fucopyranose)-1-propene (40 mg, 0.042 mmole, 1.00 mmole equiv.) in anhydrous dichloromethane (0.210 mL, 0.2M) at −78° C. was added excess ozone. The reaction contents were stirred at −78° C. for 1 hour and the reaction was terminated by the addition of dimethylsulfide and stirred for 1 hour and allowed to warm to ambient temperature. Water was added and the heterogeneous layers were separated and the organic phase was washed twice with portions of 1.0M hydrochloric acid, sodium bicarbonate and brine. The crude product was dried over anhydrous sodium sulfate, filtered and plugged through a small pad of silica gel. The solvent was removed in vacuo which afforded an oil that was plugged on Baker grade flash silica gel (47–61 mm) (ration of 50 to 1) and eluted with 50% ethyl acetate in hexane. Concentration in vacuo afforded 30 mg of 1-[3-O-(18-β-Glycyrrhetinic acid)]-2-oxo-2(tri-O-benzyl-α-L-C-methylfucopyranose)-ethane (7) (75%).

Example 8

Preparation of 1-[3-O-(18-β-Glycyrrhetinic acid)]-2-oxo-2-(α-L-C-methylfucopyranose)-ethane (8)

The following compound was prepared as described.

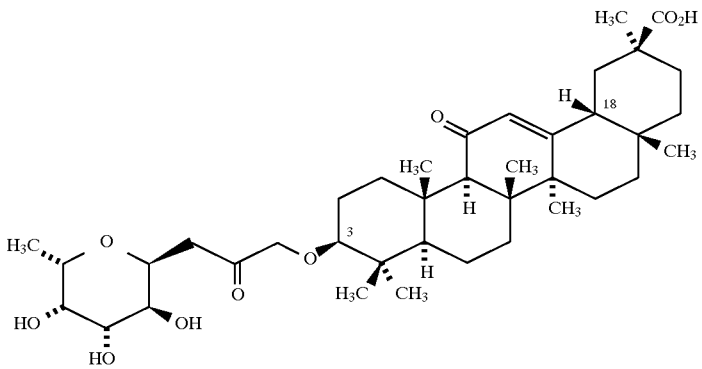

1-[3-O-(18-β-Glycyrrhetinic acid)]-2-oxo-2-(tri-O-benzyl-α-L-C-methylfucopyranose)-ethane (7) (15 mg, 0.0159 mmole, 1.00 mmole equiv.) was dissolved in 10% acetic acid in methanol (ethyl acetate can be added to enhance solubility) (1.5 mL), and 10% palladium on carbon (wetted with toluene) was added (35 mg per mmole of substrate) and placed on a Parr hydrogenation apparatus. The reaction vessel was evacuated and re-filled with hydrogen thrice and then shaken at 50 PSI for 48 hours. The reaction was terminated by filtering the contents through Celite to remove the catalyst. Concentration in vacuo and washed with dichloromethane to give 1-[3-O-(18-β-Glycyrrhetinic acid)]-2-(α-L-C-methylfucopyranose)-propane (8).

Example 9

Preparation of 1-[3-O-(18-β-Glycyrrhetinic acid)]-2-(α-L-C-methylfucopyranose)-2'-ethanol (9)

The following compound would be prepared as described.

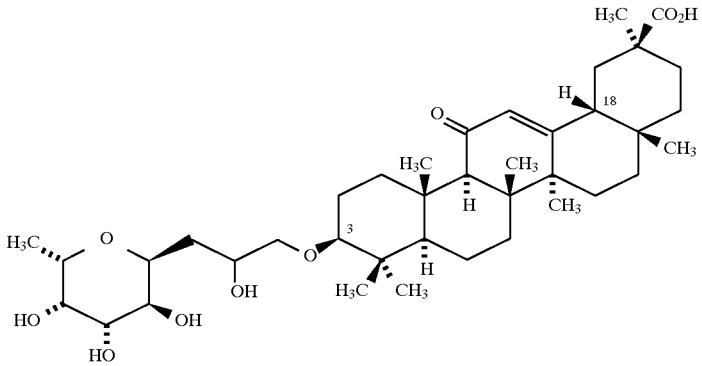

To a solution of 1-[3-O-(18-β-Glycyrrhetinic acid)]-2-oxo-2-(α-L-C-methylfucopyranose)-ethane (7) (1 g, 1.06 mmole, 1.00 mmole equiv.) in anhydrous tetrahydrofuran (5.3 mL, 0.2M) at 0° C. is added R or S-Alpine-Hydride (4.24 mL of 0.5M solution in THF 2.12 mmole, 2 mmole equiv.) and the reaction is stirred for 8 hours. The reaction is terminated by the addition of $H_2O_2$ and NaOH at 0° C. and the reaction contents are stirred for 2 hours and then over night at ambient temperature (12 hours). The reaction is diluted with ethyl acetate. The heterogeneous layers are separated and the organic phase is washed twice with portions of 25% aqueous sodium metasulfite, 1.0M hydrochloric acid, sodium bicarbonate and brine. The crude product is dried over anhydrous sodium sulfate, filtered and plugged through a small pad of silica gel. The solvent is removed in vacuo which affords an oil that is chromatographed on Baker grade flash silica gel (47–61 mm) (ration of 50 to 1) and eluted with 50% ethyl acetate in hexane and then 5% methanol in chloroform. Concentration in vacuo affords 1-[3-O-(18-β-Glycyrrhetinic acid)]-2-(tri-O-benzyl-(α-L-C-methylfucopyranose)-2'-ethanol. References:Miyano, M., Stealy, M. A., *Chem. Commun.* (1973) 180. Schaub, R. E., Weiss, M. J., *Tetrahedron Lett.* (1973) 129. Gnudzinskas, C. V., Weiss, M. J., *Tetrahedron Lett.* (1973) 141. Alpine-Hydride are used for chiral reductions of ketones see:*J. Org. Chem.* (1977) 42:2534.

Finally, 1- [3-O-(18-β-Glycyrrhetinic acid)]-2-(tri-O-benzyl-α-L-C-methylfucopyranose)-2'-ethanol (1.0 g, 1.06 mmole, 1.00 mmole equiv.) is dissolved in 10% acetic acid in methanol (0.2M) to which is added 10% palladium on carbon (35 mg per mmole of substrate) place on a Parr hydrogenation apparatus. The reaction vessel is evacuated and re-filled with hydrogen thrice and then shake at 50 PSI for 48 hours. The reaction is terminated by filtering the contents through Celite to remove the catalyst. Concentration in vacuo affords 1-[3-O-(18-β-Glycyrrhetinic acid)]-2-(α-L-C-methylfucopyranose)-2'-ethanol (9) as a white powder which is filtered and rinsed with dichloromethane.

Example 10

Anti-inflammatory Effects

Hereinafter, reference to certain of the invention compounds synthesized as described above, will be by their associated numbers in the examples and/or by their chemical name.

Using the arachidonic acid (AA), murine skin inflammation model, described by Harris, R. R. et al. (*Skin Pharmacol* (1990) 3:29–40) the anti-inflammatory activity of 1-[3-O-(18-β-Glycyrrhetinic acid)]-2-(α-L-C-methylfucopyranose)-2',3'-propanediol (5) was tested. For comparison, 18-β-glycyrrhetinic acid was also tested. All compounds were dissolved at 100 mg/mL in methanol or chloroform (18-β-glycyrrhetinic acid) except compound (5) which was at 0.80 mg/mL. 10 uL of each compound was applied to the ear. AA was applied alone, or followed immediately with 1-[3-O-(18-β-Glycyrrhetinic acid)]-2-(α-L-C-methylfucopyranose)-2',3'-propanediol (5) or 18-β-glycyrrhetinic acid. 90 minutes later a 6 mm disk of each ear was removed and weighed. It was observed that the percent inhibition of swelling caused by AA alone was reduced by about 71% for the 1-[3-O-(18-β-Glycyrrhetinic acid)]-2-(α-L-C-methylfucopyranose)-2',3'-propanediol (5) and about 61% for 1-[3-O-(18-β-Glycyrrhetinic acid)]-2-(α-L-C-methylfucopyranose)-propane (3) while only about 38% for 18-β-glycyrrhetinic acid and about 5.5% for Glycyrrhizin. Further experiments, not shown in Table 1, have shown compound (8) to have activity similar to compounds (3) and (5).

It is thus apparent that compounds (3),(5) and (8) have significant anti-inflammatory activity, and consequently are potent medicaments for treating or preventing a wide spectrum of diseases having an inflammatory component.

TABLE 1

Anti-Inflammatory Activities of Triterpenoid Acid Derivatives
Topical Administration in Arachidonic Acid Ear Model

| Compound | % Inhibition of Swelling | Amount Applied |
|---|---|---|
| Glycyrrhizin | 5.5% | 1 mg |
| 18-β-glycyrrhetinic acid | 38.9% | 1 mg |
| (3) | 61.2% | 1 mg |
| (5) | 71.3% | 800 μg |

Example 11

Effect of Triterpenoid Acid Derivatives On Cell Adhesion to E-Selectin

Experiments were conducted to determine the capacity of the invention compounds to interfere with the binding of cancer cells to E-selectin. The compounds were dissolved in dimethylformamide (DMF) prior to being assayed. The assayed consisted of combining the appropriate test compound, E-Selectin chimera which contains an IgG tail, and a detection system consisting of biotinylated anti-human Ig (Fc specific), and streptavidin-alkaline phosphatase all in 10 mM Tris, 150 mM NaCL, pH 7.2–7.4, plus 1 mM $Ca^{++}$. The mixture was rotated briskly on a rotary platform at room temperature for 30–60 minutes. Particulate matter was then removed by centrifugation, and the soluble fraction was transferred onto 96-well microtiter plates containing glutaraldehyde fixed LS174T colon carcinoma cells. After 60 minutes at 37° C., plates were washed and E-selectin chimera bound to cells was quantified by addition of pNPP substrate in 1M diethanolamine buffer containing 0.1 mg/ml $MgCl_2$ at pH 9.8. Plates were developed in the dark and read at 405 nm. The $IC_{50}$ values reported are the lowest concentration from serial two-fold dilutions (quadruplicate wells at each concentration) which inhibits by 50% or more relative to the control. DMF (vehicle) typically had no effect. The results are shown in Table 2. It will be appreciated that all the compounds significantly interfere with cancer cell binding to E-selectin binding. For all but 18-beta-glycyrrhetinic acid the compounds had low $IC_{50}$ values, thus indicating their suitability for the treatment or prevention of certain forms of metastatic cancers. Moreover, these findings stress the enhanced dual pharmacophoric activity of the invention compounds since compounds (3) and (5) and have markedly lower $IC_{50}$ values relative to 18-beta-glycyrrhetinic acid.

TABLE 2

Summary of $IC_{50}$ of Compounds in Assay of E-Selectin Binding To
Fixed LS174T Colon Carcinoma Cells (Range)

| Compound | $IC_{50}$ (mM) |
|---|---|
| 18-beta-glycyrrhetinic acid | 0.125–0.5 |
| (3) | 0.06–0.125 |
| (5) | 0.06–0.125 |
| (8) | 0.06–0.25 |

Example 12

Inhibition of P-Selectin Binding by Triterpenoid Acid Derivatives

In addition to E-selectin binding, certain of the invention compounds were tested for their capacity to inhibit P-selectin binding to cancer cells, and to a chemical known to bind to P-selectin, 2,3 sLex. The following materials and procedures were used.

Compound Preparation. Compound (5) of Example 5, and compound (8) of Example 8 were solubilized in DMF to yield a 100 mM solution.

P-Selectin Detection Solutions. Goat $F(ab')_2$ anti-human IgG (Fc spec.)-biotin and streptavidin-AP were diluted 1:1000 in 1% BSA-TBS with 1 mM Ca. An Elisa assay was utilized to measure P-selectin binding to 2,3 sLex, and P-selectin was added at 300 ng/ml. An Elisa assay was also used to assay for the capacity of the invention compounds to inhibit cancer cell binding to P-selectin. HL-60 cancer cells were used, and P-selectin was added at 200 ng/ml.

Plate Preparation. 2,3 sLex was coated at 30 pmoles/well to Probind microtiter plates for Elisa. The glycolipid was added at 50 μl/well in 50% MeOH and allowed to evaporate overnight. Elisa plates and HL-60 assay plates were blocked with 5% BSA-TBS $Ca^{++}$ for more than an hour at room temperature. The plates were washed with TBS without $Ca^{++}$.

Cell Preparation. HL-60 cells were harvested by centrifugation, washed with TBS no $Ca^{++}$, counted, and the density adjusted to $2 \times 10^6$/ml in 1% BSA-TBS $Ca^{++}$.

Assay. Briefly, the assays were conducted as follows. Compounds (5) and (8) were added to P-selectin detection solutions at 4, 2, 1, 0.5, 0.25 and 0.125 mM for the HL-60 based assay, and at 2, 1, 0.5, 0.25, 0.125 and 0.063 mM for the assay involving 2,3 sLex. DMF solutions were added directly to 1% BSA/TBS-Ca for dilutions through 0.5 mM. Lower concentrations were made in serial two-fold dilutions in BSA-TBS. These solutions were incubated at room temperature on a rotating platform for 1 hour, centrifuged to pellet particulate matter, and then added in triplicate for 2,3 sLex coated plates, or quadruplicate for HL-60 cells at 50 μl/well. An equal volume of HL-60 cells was added to wells for the cell based assay. The 2,3 sLex coated plates were incubated at 37° C. for 45 minutes, washed 3× with TBS, and 50 μl of substrate added to each well. Plates with HL-60 cells were incubated at 4° C. for 1 hour, the cells pelleted by centrifugation and washed 3× with TBS. For both assays, substrate was added at 75 μl/well. After color developed to an appropriate intensity, 50 μl/well was transferred to another plate for O.D. determination at 405 nm. Although compound (5) did inhibit P-selectin binding to sLex, it was less effective than compound (8).

The results established that the $IC_{50}$ for inhibiting P-selectin binding to 2,3 sLex for compound (8) was ~125 μM; for compound (5) it was <1 and >0.5 mM. The HL-60 assay showed that compound (8) interfered with P-selectin binding to HL-60 cells in a dose dependent way. $IC_{50}$ was ~0.75 mM. Compound (5) also interfered with P-selecting binding to HL-60 cells in a dose dependent manner, but was again less effective than compound (8). $IC_{50}$ was ~2 mM.

These results confirm and extend those presented in Example 12 in that the invention compounds have a marked and significant dual pharmacophoric capacity to interfere with selectin binding generally, as shown here relating to P-selectin and in Example 12 to E-selectin. Importantly, the invention compounds interfere with the binding of human cancer cells to both P-selectin and E-selectin.

Example 13

Inhibition of 5-Lipoxygenase

5-Lipoxygenase catalyzes the oxidative metabolism of arachidonic acid to 5-hydroxyper-oxyeicosatetranoic acid (5-HPETE), the initial reaction leading to the formation of certain leukotrienes. Thus, compounds that inhibit 5-lipoxygenase will have significant medical applications that require regulating or lowering leukotriene levels. Thus, the compounds of the instant invention were assayed for their capacity to inhibit 5-lipoxygenase.

5-Lipoxygenase assays were run using a crude enzyme preparation from rat basophilic leukemia cells (RBL-1) (Shimuzu, T., Radmark, O. and Samuelsson, B. *Proc. Natl. Acad. Sci. USA* (1984) 81:698–693 and Egan, R. W. and Gale, P. H. *J. Biol. Chem.* (1985) 260:11554–11559). Test compounds were pre-incubated with the enzyme for 5 minutes at room temperature and the reaction is initiated by addition of substrate, linoleic acid. Following an 8 minute incubation at room temperature, the reaction was terminated by addition of NaOH, and absorbance read at 234 nm to determine levels of 5-HETE. Compounds were screened at 50 μM. Table 3 shows the results.

It is apparent from a review of the table that compound (5) has significantly greater inhibitory activity at both concentrations tested relative to glycyrrhizin, and has similar activity, at both concentrations, relative to 18-beta-glycyrrhetinic acid. These findings support those in the previous examples, and stress the dual pharmacophoric activity of the invention compounds.

TABLE 3

Inhibition of 5-Lipoxygenase

| Compounds | Concentration (μM) | % Inhibition |
|---|---|---|
| Glycyrrhizin | 1000 | 31 |
|  | 100 | 9 |
| 18-beta-glycyrrhetinic acid | 1000 | 81 |
|  | 100 | 36 |
| (5) | 1000 | 74 |
|  | 100 | 20 |

The instant invention is shown and described herein in what is considered to be the most practical and preferred embodiments. It is recognized, however, that departures may be made therefrom which are within the scope of the invention, and that modifications will occur to one skilled in the art upon reading this disclosure. Consequently, it will be understood that the scope of the invention is not limited other than by the scope of the following claims.

What is claimed is:

1. A method for assaying for the presence of a selectin in a sample, comprising the steps of:
    contacting the sample with a triterpenoid acid derivative which is linked to a glycoside moiety at the C-3 position of the aglycon by a three carbon linker; and
    determining the presence or absence of selectin bound to said triterpenoid acid derivative.

2. A method as in claim 1, wherein the triterpenoid acid derivative has the following structural formula:

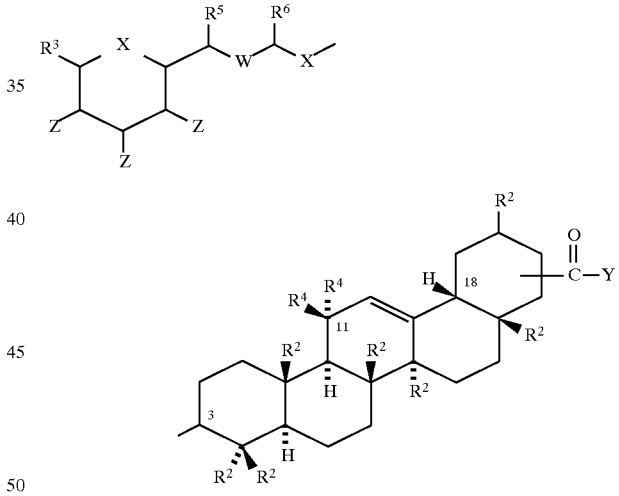

wherein Y is $OR^1$, $NR_2^1$, or O—M;
   $R^1$ is H or lower alkyl (1–4C);
   M is $H^+$, $Na^+$, $Mg^{2+}$ or $Ca^{2+}$;
   $R^2$ is $CH_2OR^1$ or $CH_3$;
   $R^3$ is H, $CH_3$, lower alkyl (1–4C), COY, $CH_2OH$, $CH_2OCH_2CH=CH_2$, or $CH_2OSO_3M$;
   Z is oxo, $NR_2^1$, $NR^1Ac$, $NR^1Bz$, H, $OCH_3$, lower alkyl (1–4C), OH, $SO_3M$, $OCH_2CH=CH_2$, $OCH_2 CO_2H$ or O-glycoside;
   $R^4$ is H, OH, $SO_3M$, $NH(CH_2)_nNH_2$ or $NHPh(NH_2)_n$ wherein n is 1,2,3,4,5,6,7 or 8 and Ph is a phenyl or naphthyl ring substituted with no more than three amine functional groups with the remaining substitutions selected from the group consisting of H, $R^1$, $R^2$ or $CO_2R^1$; or both $R^4$ taken together form an oxo group;
   $R^5$ and $R^6$ are each H;

X is O, S or $NR_2^1$; and

W is C=O, C=$CR_2^1$, $CR^1CR_3^1$, $CR^1 CR_2^1OR^1$, $COR^1CR^1OR_2^1$, $COR^1CR_2^1OR^1$, $CR^1CR_2^1NR_2^1$ or $CR^1CR_2^1OCR^1COY$.

3. A method as in claim 2 wherein $R^1$ is hydrogen, $R^2$ and $R^3$ are methyl, both $R^4$ groups together form an oxo and X is oxygen.

4. A method as in claim 3 wherein W is $C(OH)CH_2OH$.

5. A method as in claim 3 wherein W is $CHCH_3$.

6. A method as in claim 2 wherein $R^2$ and $R^3$ are methyl and X is oxygen.

7. A method as in claim 2 wherein W is $C(OH)CH_2OH$.

8. A method of determining a site of selectin in a patient in need thereof, comprising the steps of:

administering to the patient a derivative of a triterpenoid acid which is linked to a glycoside moiety at the C-3 position of the aglycon by a three carbon linker, wherein a detectable label is attached to the triterpenoid acid derivative; and detecting the presence of the labelled triterpenoid acid derivative in the patient.

9. A method as in claim 8 wherein the detectable label is a radioactive label.

10. A method as in claim 8, wherein the triterpenoid acid derivative has the following structural formula:

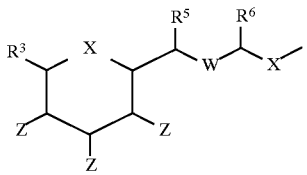

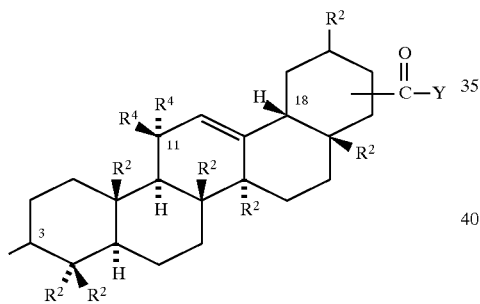

wherein Y is $OR^1$, $NR_2^1$, or O—M;

$R^1$ is H or lower alkyl (1—4C);

M is $H^+$, $Na^+$, $Mg^{2+}$ or $Ca^{2+}$;

$R^2$ is $CH_2OR^1$ or $CH_3$;

$R^3$ is H, $CH_3$, lower alkyl (1–4C), COY, $CH_2OH$, $CH_2OCH_2CH=CH_2$, or $CH_2OSO_3M$;

Z is oxo, $NR_2^1$, $NR^1Ac$, $NR^1Bz$, H, $OCH_3$, lower alkyl (1–4C), OH, $SO_3M$, $OCH_2CH=CH_2$, $OCH_2CO_2H$ or O-glycoside;

$R^4$ is H, OH, $SO_3M$, $NH(CH_2)_nNH_2$ or $NHPh(NH_2)_n$ wherein n is 1,2,3,4,5,6,7 or 8 and Ph is a phenyl or naphthyl ring substituted with no more than three amine functional groups with the remaining substitutions selected from the group consisting of H, $R^1$, $R^2$ or $CO_2R^1$; or both $R^4$ taken together form an oxo group;

$R^5$ and $R^6$ are each H;

X is O, S or $NR_2^1$; and

W is C=O, C=$CR_2^1$, $CR^1CR_3^1$, $CR^1CR_2^1OR^1$, $COR^1CR^1OR_2^1$, $COR^1CR_2^1OR^1$, $CR^1CR_2^1NR_2^1$ or $CR^1CR_2^1OCR^1COY$.

11. A method as in claim 10 wherein $R^1$ is hydrogen, $R^2$ and $R^3$ are methyl, both $R^4$ groups together form an oxo and X is oxygen.

12. A method as in claim 11 wherein W is $C(OH)CH_2OH$.

13. A method as in claim 11 wherein W is $CHCH_3$.

14. A method as in claim 10 wherein $R^2$ and $R^3$ are methyl and X is oxygen.

15. A method as in claim 10 wherein W is $C(OH)CH_2OH$.

16. A method of determining a site of selectin mediated inflammation in a patient in need thereof, comprising the steps of:

administering to the patient a derivative of a triterpenoid acid, wherein a detectable label is attached to the triterpenoid acid derivative and wherein the triterpenoid acid derivative has the following structural formula:

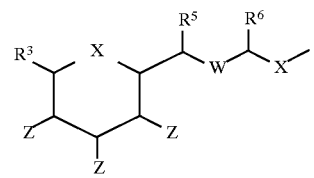

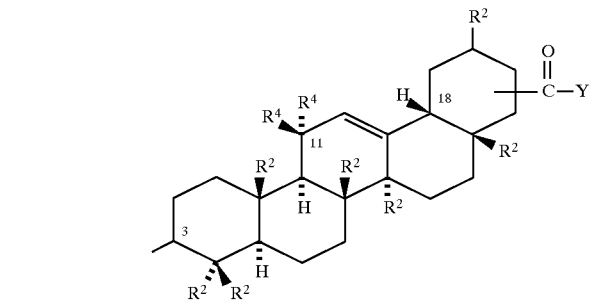

wherein Y is $OR^1$, $NR_2^1$, or O—M;

$R^1$ is H or lower alkyl (1–4C);

M is $H^+$, $Na^+$, $Mg^{2+}$ or $Ca^{2+}$;

$R^2$ is $CH_2OR^1$ or $CH_3$;

$R^3$ is H, $CH_3$, lower alkyl (1–4C), COY, $CH_2OH$, $CH_2OCH_2CH=CH_2$, or $CH_2OSO_3M$;

Z is oxo, $NR_2^1$, $NR^1Ac$, $NR^1Bz$, H, $OCH_3$, lower alkyl (1–4C), OH, $SO_3M$, $OCH_2CH=CH_2$, $OCH_2 CO_2H$ or O-glycoside;

$R^4$ is H, OH, $SO_3M$, $NH(CH_2)_nNH_2$ or $NHPh(NH_2)$, wherein n is 1,2,3,4,5,6,7 or 8 and Ph is a phenyl or naphthyl ring substituted with no more than three amine functional groups with the remaining substitutions selected from the group consisting of H, $R^1$, $R^2$ or $CO_2R^1$; or both $R^4$ taken together form an oxo group;

$R^1$ and $R^6$ are each H;

X is O, S or $NR_2^1$; and

W is C=O, C=$CR_2^1$, $CR^1CR_3^1$, $CR^1CR_2^1OR^1$, $COR^1CR^1OR_2^1$, $COR^1CR_2^1OR^1$, $CR^1CR_2^1NR_2^1$ or $CR^1CR_2^1OCR^1COY$; and detecting the presence of the labelled triterpenoid acid derivative in the patient.

17. A method as in claim 16 wherein $R^1$ is hydrogen, $R^2$ and $R^3$ are methyl, both $R^4$ groups together form an oxo and X is oxygen.

18. A method as in claim 17 wherein W is selected from the group consisting of $C(OH)CH_2OH$ and $CHCH_3$.

19. A method as in claim 16 wherein $R^2$ and $R^3$ are methyl and X is oxygen.

20. A method as in claim 16 wherein W is selected from the group consisting of $C(OH)CH_2OH$ and $CHCH_3$.

* * * * *